(12) United States Patent
Zhao

(10) Patent No.: US 9,827,184 B2
(45) Date of Patent: Nov. 28, 2017

(54) PEELABLE TRANSPARENT DIAMOND NAIL-CARE COAT

(71) Applicant: LES FINS NETWORK TECHNOLOGY CO.,LTD., Hangzhou (CN)

(72) Inventor: Ming Zhao, Hangzhou (CN)

( * ) Notice: Subject to any disclaimer, the term of this patent is extended or adjusted under 35 U.S.C. 154(b) by 0 days.

(21) Appl. No.: 15/188,981

(22) Filed: Jun. 22, 2016

(65) Prior Publication Data

US 2017/0035671 A1   Feb. 9, 2017

Related U.S. Application Data

(63) Continuation of application No. PCT/CN2015/095157, filed on Nov. 20, 2015.

(30) Foreign Application Priority Data

Aug. 3, 2015 (CN) .......................... 2015 1 0469372

(51) Int. Cl.
| | |
|---|---|
| A61K 8/49 | (2006.01) |
| A61K 8/81 | (2006.01) |
| A61K 8/35 | (2006.01) |
| A61K 8/37 | (2006.01) |
| A61K 8/891 | (2006.01) |
| A61K 8/19 | (2006.01) |
| A61K 8/26 | (2006.01) |
| A61K 8/34 | (2006.01) |
| A61K 8/60 | (2006.01) |
| A61K 8/73 | (2006.01) |
| A61K 8/362 | (2006.01) |
| A61K 8/27 | (2006.01) |
| A61Q 3/02 | (2006.01) |
| A61K 8/29 | (2006.01) |

(52) U.S. Cl.
CPC ................ *A61K 8/891* (2013.01); *A61K 8/35* (2013.01); *A61K 8/37* (2013.01); *A61K 8/49* (2013.01); *A61K 8/8147* (2013.01); *A61Q 3/02* (2013.01); *A61K 2800/262* (2013.01); *A61K 2800/594* (2013.01); *A61K 2800/95* (2013.01)

(58) Field of Classification Search
None
See application file for complete search history.

*Primary Examiner* — Melissa Fisher
(74) *Attorney, Agent, or Firm* — Wayne & Ken, LLC; Tony Hom

(57) ABSTRACT

The present invention relates to a peelable transparent diamond nail-care coat. The peelable transparent diamond nail-care coat mainly contains the following components in parts by weight: 40-50 parts of polyacrylate-2-cross-linked polymer, 5-12 parts of benzophenone, 20-30 parts of ethyl methacrylate, 8-16 parts of polydimethylsiloxane, 0.01-0.05 part of a compound of formula I, and 10-15 parts of trimethylolpropane triacrylate. The nail-care coat disclosed by the present invention can be cured to form a film only by being subjected to LED light curing for 1 to 2 minutes, and is stable in performance and washable, without a pungent smell, and healthy and environment-friendly; and the nail-care coat disclosed by the present invention is a two-in-one product composed of a prime coat and a top coat, and is capable of being peeled or torn as a whole, without the need of washing and without residue.

9 Claims, No Drawings

PEELABLE TRANSPARENT DIAMOND NAIL-CARE COAT

CROSS-REFERENCE TO RELATED APPLICATIONS

This application is a continuation of International Patent Application No. PCT/CN20151095157 with a filing date of Nov. 20, 2015, designating the United States, now pending, and further claims priority to Chinese Patent Application No. 201510469372.3 with a filing date of Aug. 3, 2015. The content of the aforementioned applications, including any intervening amendments thereto, are incorporated herein by reference.

TECHNICAL FIELD

The present invention relates to the field of cosmetic synthetic generation, and particularly relates to a peelable transparent diamond nail-care coat.

BACKGROUND OF THE PRESENT INVENTION

Nail polish is also known as 'nail varnish', and is a major type of products in make-up products. People who care their beauty apply the nail polish onto nails, and then the nails are colorful, shiny and bright; therefore, the nail polish is a make-up product which is very popular among women of all ages. The nail polish existing on the market at present has various brands and is of varying quality.

CN 102908266A (Feb. 6, 2013) discloses environmental-friendly hail polish and a preparation method thereof. The environmental-friendly nail polish comprises an emulsion, a film-forming agent, water-based environmental-friendly color paste and deionized water, wherein monomers for preparing the emulsion comprise butyl acrylate, vinyl benzene, methacrylic acid and vinyl hydroxyl silicone oil; and an initiator is azodiisobutyronitrile. The patent claims that the nail polish is environment-friendly nail polish, but this is not true.

CN 102552059A (Jul. 11, 2012) discloses low-irritation nail polish. The nail polish is formed by taking alcohol solvents and alcohol film-forming agents as main materials, and stirring and mixing the main materials with a thickening agent, a suspending agent, a plasticizer, a paint box essence and other additives. However, the nail polish has quite high irritation, and also causes a burning sensation and injury to a certain extent in case of contacting with the skin.

Meanwhile, the prior art has not disclosed a nail-care prime coat which is healthy and environment-friendly, and easy to peel or tear.

SUMMARY OF PRESENT INVENTION

The objective of the present invention is to provide a peelable transparent diamond nail-care coat. The peelable transparent diamond nail-care coat is quick in drying, easy to peel or tear, stable in performance and washable, convenient to meet the needs of different occasions and different colors at any time and any place, without a pungent smell, healthy and environment-friendly, and capable of achieving no residue without the need of washing.

The above-mentioned technical objective of the present invention is realized through the following technical solution:

a peelable transparent diamond nail-care coat contains the following components in parts by weight:
- 40-50 parts of polyacrylate-2-cross-linked polymer,
- 5-12 parts of benzophenone,
- 20-30 parts of ethyl methacrylate,
- 8-16 parts of polydimethylsiloxane,
- 0.01-0.05 part of a compound of formula I, and
- 10-15 parts of trimethylolpropane triacrylate, wherein the compound of formula I is shown as the following formula:

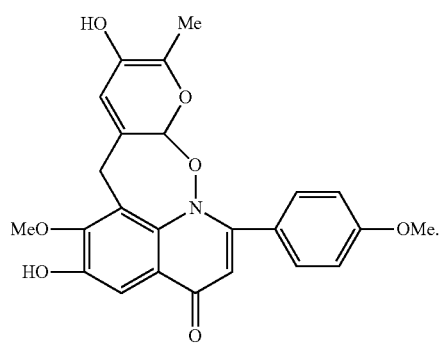

The polydimethylsiloxane in the present invention is an organosilicone, has high chemical stability and physiological activity, and is a material which is healthy and environment-friendly for human bodies; and the polydimethylsiloxane plays the roles of a levelling agent, a mould release agent and a defoaming agent in the nail-care coat disclosed by the present invention.

The nail-care coat disclosed by the present invention can be used as a base prime coat before nail cosmetology, and has a nail-care effect: after being applied on nails, the nail-care coat can be cured to form a film only by being subjected to LED light curing for 1 to 2 minutes, and has a transparent diamond-like gloss; the existing peelable water-based nail polish has the worst shortcoming of being liable to dissolve in water, whereas the nail-care coat disclosed by the present invention is stable in performance and washable, without a pungent smell, and healthy and environment-friendly; the nail-care coat disclosed by the present invention is a two-in-one product composed of a prime coat and a sealing layer, and capable of being peeled or torn as a whole, without the need of washing and without residue; and the nail-care coat disclosed by the present invention is capable of improving the saturability, brightness and durability of colors in case of being used as the sealing layer.

The nail-care coat disclosed by the present invention can also be directly used as a transparent color except being used as a colorless base prime coat before nail cosmetology; and moreover, the nail-care coat has excellent anti-wear performance and fullness, and achieves an effect of combining nail care with nail cosmetology.

Preferably, the nail-care coat contains one or a pigment-filler mixture of titanium dioxide, kaolin and color paste.

Preferably, the nail-care coat contains 6-9 parts of first composite regulator and 7-11 parts of second composite regulator;

the first composite regulator comprises a mixture composed of polyglycerol-2-triisostearate, glycerol and ammonium acryloyldimethyltaurate/VP copolymer according to a mass ratio of 1:(3 to 4):(1 to 2); and the second composite regulator comprises a mixture composed of diisostearyl malate, silica silylate and butyl methoxydibenzoylmethane according to a mass ratio of 1:(2 to 4):(1 to 3).

The first composite regulator in the present invention has excellent dispersion, thickening, and anti-friction and anti-wear performance after being proportioned; the second composite regulator has antioxidant and smooth functions after being proportioned; the two composite regulators can achieve a synergistic effect in case of being combined together. The nail-care coat composed of the components according to the proportions in the present invention has both resistance to high temperature (above 30° C.) and resistance to low temperature (below −10° C.), and the prepared nail-care coat can be used in many special occasions such as hot beaches or cold north, and keeps stable performance.

More preferably, the nail-care coat contains 3-7 parts of third composite regulator; and the third composite regulator comprises a mixture composed of chitosan with a deacetylation degree of 70%-80%, oligosaccharide with a molecular weight of 1800 Daltons-2000 Daltons, and DPnB according to a mass ratio of 1:(0.5 to 0.8):(1.3 to 1.7).

Wherein, DPnB is dipropylene glycol monobutyl ether. The third composite regulator in the present invention has high film-forming and anti-wear performance; live hydroxyl groups and amino groups are contained in macromolecules of chitosan, have high chemical reaction capacities, and give many excellent chemical properties and a physiological activity to the chitosan, and excessive degradation of the chitosan can be prevented due to the mutual cross-linking action of an oligosaccharide layer and a chitosan layer; the three composite regulators can achieve a synergistic effect in case of being combined together; and meanwhile, the chitosan can also play a synergistic role with polydimethylsiloxane which also has a high physiological activity.

More preferably, a preparation method for the chitosan with the deacetylation degree is as follows: carrying out heating treatment on chitin in alkaline liquor with a mass concentration of 40%-50% for 1 h-2 h at 130° C.-150° C.; so as to prepare the chitosan with a deacetylation degree of 70%-80%, and a molecular weight of 20000 Daltons-35000 Daltons.

The chitin is a natural high-polymer material extracted from the shells of shrimps, crabs and other crustaceans, and the cell walls of mushrooms, alga and other lower plants, is the second major bio-derived resource ranking second only to cellulose in the natural world, has a wide source, and is an excellent renewable resource. In the face of increasing scarcity of resources nowadays, adequate utilization for novel renewable resources becomes more important, and chitin attracts much attention due to the excellent performance and renewable capacity thereof; and the chitin, the chitosan and their derivatives all have a great inhibition effect on bacteria, yeasts, fungi and other microorganisms.

Preferably, a preparation method for the polyacrylate-2-cross-linked polymer is as follows:

(1) preparing, in parts by weight, 30-40 parts of polymer P(MMA-MAh)-PEG6000 and 40-60 parts of regulating solution to form a primarily-mixed solution; the regulating solution is propylene carbonate solution comprising sodium perchlorate with a concentration of 0.4 mol/L-0.7 mol/L, and N-butyl benzimidazole with a concentration of 0.3 mol/L-0.8 mol/L; in the polymer P(MMA-MAh)-PEG6000, MMA is methyl methacrylate. MAh is maleic anhydride, P(MMA-MAh) is a copolymer of methyl methacrylate and maleic anhydride, and PEG6000 is polyethylene glycol with a molecular weight of 6000;

(2) adding 2-7 parts of dodecahydroxyl stearic acid in the primarily-mixed solution, and heating to 30° C.-45° C. and reacting for 5 min-9 min under the protection of nitrogen;

(3) rinsing with deionized water and drying to obtain the polyacrylate-2-cross-linked polymer.

The polyacrylate-2-cross-linked polymer prepared by the preparation method in the present invention has excellent film-forming performance, thermal performance and dimensional stability, so that the nail-care coat is quick in drying, easy to peel or tear, enough in brightness, without a pungent smell healthy and environment-friendly, stable in performance and washable, and capable of being peeled or torn as a whole after use, without the need of washing and without residue.

Preferably, the nail-care coat contains 1-4 parts of fourth composite regulator; and the fourth composite regulator is composed of the following raw materials in parts by weight:

25-35 parts of cetyl octanoate, 15-18 parts of glutaric acid, 0 parts of butantriol, 5-7 parts of zinc oxide, 3-5 parts of magnesium oxide, 15-25 parts of chloroprene rubber, 70-95 parts of elastic gum, 2-3 parts of softening oil, 15-20 parts of dimethyl carbonate and 20-30 parts of ethylbenzene;

the elastic gum comprises a first elastic gum and a second elastic gum which are mixed according to a weight ratio of (1 to 3):1;

the first elastic gum comprises 10-35 parts by weight of acrylic resin emulsion with a solid content of 60%-75%, 10-15 parts of waterborne polyurethane, 5-8 parts by weight of acrylic resin powder, 2-6 parts by weight of EVA emulsion with a solid content of 20%-35% and 1-4 parts by weight of chlorinated polypropylene;

a preparation method for the second elastic gum is as follows: heating 1-5 parts of polyvinyl alcohol aqueous solution with a mass concentration of 20%-25% and 20-30 parts of 15 wt %-20 wt % waterborne polyurethane aqueous solution to 60° C.-80° C., cooling to 30° C.-50° C. and adding 10-15 parts of acrylate, then adding 0.1-0.2 part of lithium hydroxide and heating to 100° C.-110° C., then adding 5-8 parts of sclerotin protein, 6-9 parts of abietin and 2-4 parts of eugenol; and reacting for 3 to 5 hours and cooling to 45° C.-55° C., then adding 6-8 parts of bamboo charcoal micro-powder, 2-7 parts of anion powder and 10-13 parts of octylphenol polyoxyethylene ether, stirring for 1 to 1.5 hours, and cooling to prepare the second elastic gum.

The fourth composite regulator in the present invention has the advantages of high initial adhesion and high fastness; through addition of the fourth composite regulator, the nail-care transparent coat disclosed by the present invention has an effect of combining a prime coat with a sealing layer, and is peelable or tearable when in use, without a pungent smell, healthy and environment-friendly, stable in performance and washable, and capable of being peeled or torn as a whole after use, without the need of washing and without residue.

A preparation method for a peelable transparent diamond nail-care coat comprises the steps of sequentially adding 20-30 parts of ethyl methacrylate, 8-16 parts of polydimethylsiloxane, 0.01-0.05 part of compound of formula I, 10-15 parts of trimethylolpropane triacrylate, 40-50 parts of polyacrylate-2-cross-linked polymer, and 5-12 parts of benzophenone, and mixing the above-mentioned ingredients, and then uniformly stirring and mixing at a high speed to prepare the nail-care coat.

The inventor found that during mixing and stirring preparation for the nail-care transparent coat, the adding sequence of the ingredients affects the performance of the product. The nail-care transparent coat prepared according to the adding sequence in the method in the present invention is higher in stability and anti-wear performance in case of meeting a requirement of being easier to peel or tear.

Preferably, after the above-mentioned substances are added in sequence, a second composite regulator is added and stirred for 10 min-15 min, and then a first composite regulator is added and stirred continuously for 3 min-6 min; then a fourth composite regulator is added and stirred continuously for 2 min-5 min; and finally a third composite regulator is added and stirred continuously for 1 min-4 min, and filtering and packaging are carried out to obtain the finished product.

In summary, the present invention has the following beneficial effects:

1. after being applied on nails, the nail-care coat disclosed by the present invention can be cured to form a film only by being subjected to LED light curing for 1 to 2 minutes; the nail-care coat is stable in performance and washable, and capable of being peeled or torn as a whole after use, without the need of washing and without residue; and the nail-care coat is convenient to meet the needs of different occasions and different colors at any time and any place, without a pungent smell, and healthy and environment-friendly;

2. the nail-care coat disclosed by the present invention can be directly used as a transparent color, has excellent anti-wear performance and fullness, and achieves an effect of combining nail care with nail cosmetology;

3. the nail-care transparent coat disclosed by the present invention has a great inhibition effect on bacteria, yeasts, fungi and other microorganisms, and is healthy and environment-friendly;

4. the nail-care coat composed of the components according to the proportions in the present invention has both resistance to high temperature (above 30° C.) and resistance to low temperature (below −10° C.), and the prepared nail-care coat can be used in many special occasions such as hot beaches or cold north, and keeps stable performance;

5. the compound of formula I and extracted from ginkgo leaves is added in the formula of the present invention, and is capable of effectively preventing generation of nail fungi;

6. the nail-care transparent coat disclosed by the present invention has an effect of combining a prime coat with a sealing layer.

DETAILED DESCRIPTION OF PREFERRED EMBODIMENTS

The present invention is further illustrated below through embodiments. It should be understood that, the methods of the embodiments of the present invention are merely used for illustrating the present invention, but the present invention is not limited thereto, and simple improvements on the preparation methods of the present invention on the premise of the conception of the present invention shall all fall within the scope of protection of the present invention. All raw materials, solvents and strains used in the embodiments are purchased from the company of Sigma Biochemical and Organic Compounds for Research and Diagnostic Clinical Reagents.

Preparation Embodiment for the Compound of Formula I:

Ginkgo leaf tablets are taken as raw materials, crushed, soaked ethanol, and extracted for 2 to 4 times and for 12 h-17 h every time, and extraction solution is combined, filtered and concentrated to obtain a ginkgo leaf extract wherein ethanol:ginkgo leaves=(3 to 4):1, by weight ratio.

The above-mentioned ginkgo leaf extract is dissolved with acetone, then mixed with 60-120-mesh silica gel which is 2-5 times by weight than the extract, then subjected to dry-method column packing, and then subjected to gradient elution with gradient chloroform-methanol solution in a volume ratio of 9:1, 8:2, 7:3, 6:4 and 5:5 sequentially, and an eluent obtained during elution with the chloroform-methanol solution in a volume ratio of 9:1 is collected, and is called as a first eluent. The above-mentioned first eluent is separated continuously with a silica gel chromatography column, and subjected to gradient elution with chloroform-acetone solution in a volume ratio of 15:1, 10:1, 5:1 and 2:1 sequentially, and an eluent obtained during elution with the chloroform-acetone solution in a volume ratio of 10:1 is called as a second eluent. The above-mentioned second eluent is separated continuously with a silica gel chromatography column, and subjected to gradient elution with petroleum ether-ethyl acetate solution in a volume ratio of 9:1, 8:2, 7:3, 6:4 and 5:5 sequentially, and an eluent obtained during elution with the petroleum ether-ethyl acetate solution in a volume ratio of 7:3 is called as third eluent.

The above-mentioned third eluent is charged in a high pressure liquid chromatography (reversed phase preparative chromatography with a pressure of 5 Mpa-15 Mpa) and subjected to separation and purification, in the high pressure liquid chromatography, a $C_{18}$ chromatographic column with specifications of 21.2 mm×250 mm and 5 μm is used, a mobile phase is 60 wt % methanol aqueous solution, a flow rate of the mobile phase is 12 mL/min, and a detection wavelength of an ultraviolet detector is 374 nm; 60-150 μL of a ample is injected for the third eluent every time, the eluent corresponding to the case that a chromatographic peak retention time is 31 min after each sample injection, is collected, and the compound of formula I

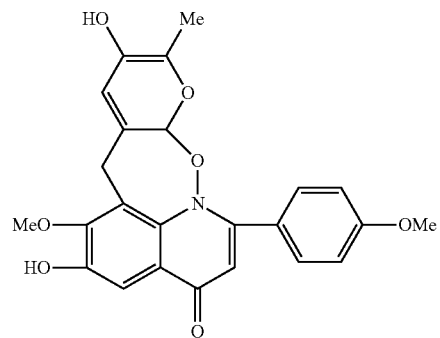 [SMILES: COc1ccc(-c2cc(=O)c3cc(O)c(OC)c4c3n2OC2OC(C)=C(O)C=C2C4)cc1]

is obtained after solvent removal.

After being obtained, the above-mentioned compound of formula I may be re-dissolved in methanol solution, the methanol solution is taken as a mobile phase, and chromatographic separation is carried out through a gel column. In this way, the compound of formula I can be further purified.

The compound of formula I in the present invention is yellow powder; and the main structural feature peaks of an ultraviolet spectrum, an infrared spectrum and H-nuclear magnetic resonance of the compound of formula I are listed below.

The ultraviolet spectrum (with a solvent of methanol): $\lambda_{max}$(log ε)210(4.36) nm, $\lambda_{max}$(log ε)266(3.82) nm and $\lambda_{max}$(log ε)374(3.68) nm;

the infrared spectrum (with potassium bromide tablets): $v_{max}$3452 cm$^{-1}$, $v_{max}$2924 cm$^{-1}$, $v_{max}$2615 cm$^{-1}$, $v_{max}$1668 cm$^{-1}$, $v_{max}$1612 cm$^{-1}$, $v_{max}$1516 cm$^{-1}$, $v_{max}$1437 cm$^{-1}$, $v_{max}$1316 cm$^{-1}$, $v_{max}$1247 cm$^{-1}$, $v_{max}$1182 cm$^{-1}$, $v_{max}$1083 cm$^{-1}$, $v_{max}$1022 cm$^{-1}$, $v_{max}$868 cm$^{-1}$ and $v_{max}$722 cm$^{-1}$;

$^1$H NMR (500 MHz, CDCl$_3$, ppm) δ: 10.7 (s —OH), 9.48 (s —OH) 6.28-7.52 (d, —CH 5H), 6.57 (s, 1H), 6.18 (s 1H), 3.27 (d, —CH$_2$), 1.99-3.81 (d, —CH$_3$ 9H).

Preparation Embodiments for the Nail-Care Coat:

The formula 1 of the first composite regulator: formed by mixing polyglycerol-2-triisostearate, glycerol and ammonium acryloyldimethyltaurate/VP copolymer according to a mass ratio of 1:3:2.

The formula 2 of the first composite regulator: formed by mixing polyglycerol-2-triisostearate, glycerol and ammonium acryloyldimethyltaurate/VP copolymer according to a mass ratio of 1:4:1.

The formula 3 of the first composite regulator: formed by mixing polyglycerol-2-triisostearate, glycerol and ammonium acryloyldimethyltaurate/VP copolymer according to a mass ratio of 1:3:1.

The formula 1 of the second composite regulator: formed by mixing diisostearyl malate, silica silylate and butyl methoxydibenzoylmethane according to a mass ratio of 1:2:3.

The formula 2 of the second composite regulator: formed by mixing diisostearyl malate, silica silylate and butyl methoxydibenzoylmethane according to a mass ratio of 1:4:1.

The formula 3 of the second composite regulator: formed by mixing diisostearyl malate, silica silylate and butyl methoxydibenzoylmethane according to a mass ratio of 1:3:2.

The formula 1 of the third composite regulator: formed by mixing chitosan with a deacetylation degree of 70%, oligosaccharide with a molecular weight of 1800 Daltons, and DPnB according to a mass ratio of 1:0.5:1.7.

The formula 2 of the third composite regulator: formed by mixing chitosan with a deacetylation degree of 80%, oligosaccharide with a molecular weight of 2000 Daltons, and DPnB according to a mass ratio of 1:0.8:1.3.

The formula 3 of the third composite regulator: formed by mixing chitosan with a deacetylation degree of 75%, oligosaccharide with a molecular weight of 1900 Daltons, and DPnB according to a mass ratio of 1:0.6:1.5.

The formula 1 of the fourth composite regulator: 30 parts of cetyl octanoate, 17 parts of glutaric acid, 9 parts of butantriol, 6 parts of zinc oxide, 4 parts of magnesium oxide, 20 parts of chloroprene rubber, 85 parts of elastic gum, 2.3 parts of softening oil 18 parts of dimethyl carbonate and 25 parts of ethylbenzene;

the elastic gum comprises a first elastic gum and a second elastic gum which are mixed according to a weight ratio of 1:3;

the first elastic gum comprises 25 parts by weight of acrylic resin emulsion with a solid content of 68%, 12 parts of waterborne polyurethane, 6 parts by weight of acrylic resin powder, 4 parts by weight of EVA emulsion with a solid content of 29% and 3 parts by weight of chlorinated polypropylene.

The formula 2 of the fourth composite regulator: 25 parts of cetyl octanoate, 15 parts of glutaric acid, 3 parts of butantriol, 5 parts of zinc oxide, 3 parts of magnesium oxide, 15 parts of chloroprene rubber, 70 parts of elastic gum, 2 parts of softening oil, 15 parts of dimethyl carbonate and 30 parts of ethylbenzene;

the elastic gum comprises a first elastic gum and a second elastic which are mixed according to a weight ratio of 1:2;

the first elastic gum comprises 10 parts by weight of acrylic resin emulsion with a solid content of 60%, 10 parts of waterborne polyurethane, 5 parts by weight of acrylic resin powder, 2 parts by weight of EVA emulsion with a solid content of 20% and 4 parts by weight of chlorinated polypropylene.

The formula 3 of the fourth composite regulator: 35 parts of cetyl octanoate, 18 parts of glutaric acid, 10 parts of butantriol, 7 parts of zinc oxide, 5 parts of magnesium oxide, 25 parts of chloroprene rubber, 95 parts of elastic gum, 3 parts of softening oil, 20 parts of dimethyl carbonate and 20 parts of ethylbenzene;

the elastic gum comprises a first elastic gum and a second elastic gum which are mixed according to a weight ratio of 1:3;

the first elastic gum comprises 35 parts by weight of acrylic resin emulsion with a solid content of 75%, 15 parts of waterborne polyurethane, 8 parts by weight of acrylic resin powder, 6 parts by weight of EVA emulsion with a solid content of 35% and 1 part by weight of chlorinated polypropylene.

Embodiment I

A peelable transparent diamond nail-care coat contains the following components in parts by weight:
40 parts of polyacrylate-2-crosslinked polymer,
5 parts of benzophenone,
20 parts of ethyl methacrylate,
8 parts of polydimethylsiloxane,
0.01 part of compound of formula I, and
15 parts of trimethylolpropane triacrylate.

The above-mentioned ingredients are mixed, and then uniformly stirred and mixed at a high speed to prepare the nail-care coat, A preparation method for the polyacrylate-2-cross-linked polymer is as follows:

(1) preparing, in parts by weight, 30 parts of polymer P(MMA-MAh)-PEG6000 and 40 parts of regulating solution to form a primarily-mixed solution; the regulating solution is propylene carbonate solution comprising sodium perchlorate with a concentration of 0.4 mol/L and N-butyl benzimidazole with a concentration of 0.8 mol/L; in the polymer P(MMA-MAh)-PEG6000, MMA is methyl methacrylate, MAh is maleic anhydride, P(MMA-MAh) is a copolymer of methyl methacrylate and maleic anhydride, and PEG6000 is polyethylene glycol with a molecular weight of 6000;

(2) adding 2 parts of dodecahydroxyl stearic acid in the primarily-mixed solution, and heating to 30° C. and reacting for 5 min-9 min under the protection of nitrogen;

(3) rinsing with deionized water and drying to obtain the polyacrylate-2-cross-linked polymer.

Embodiment II

A peelable transparent diamond nail-care coat contains the following components in parts by weight:
50 parts of polyacrylate-2-cross-linked polymer,
12 parts of benzophenone,
30 parts of ethyl methacrylate,
16 parts of polydimethylsiloxane,
0.02 part of compound of formula I, and
10 parts of trimethylolpropane triacrylate, The above-mentioned ingredients are mixed, and then uniformly stirred and mixed at a high speed to prepare the nail-care coat.

A preparation method for the polyacrylate-2-cross-linked polymer is as follows:

(1) preparing, in parts by weight, 40 parts of polymer P(MMA-MAN-PEG6000 and 60 parts of regulating solution to form a primarily-mixed solution; the regulating solution is propylene carbonate solution comprising sodium perchlorate with a concentration of 0.7 mol/L and N-butyl benzimidazole with a concentration of 0.3 mol/L; in the polymer P(MMA-MAh)-PEG6000, MMA is methyl methacrylate, MAh is maleic anhydride, P(MMA-MAh) is a copolymer of methyl methacrylate and maleic anhydride, and PEG6000 is polyethylene glycol with a molecular weight of 6000;

(2) adding 7 parts of dodecahydroxyl stearic acid in the primarily-mixed solution, and heating to 45° C. and reacting for 9 min under the protection of nitrogen;

(3) rinsing with deionized water and drying to obtain the polyacrylate-2-cross-linked polymer.

Embodiment III

A peelable transparent diamond nail-care coat contains the following components in parts by weight:
45 parts of polyacrylate-2-cross-linked polymer,
7 parts of benzophenone,
25 parts of ethyl methacrylate,
10 parts of polydimethylsiloxane,
0.03 part of compound of formula I, and
12 parts of trimethylolpropane triacrylate.

The above-mentioned ingredients are mixed, and then uniformly stirred and mixed at a high speed to prepare the nail-care coat.

A preparation method for the polyacrylate-2-cross-linked polymer is as follows:

(1) preparing, in parts by weight, 30-40 parts of polymer P(MMA-MAh)-PEG6000 and 50 parts of regulating solution to form a primarily-mixed solution; the regulating solution is propylene carbonate solution comprising sodium perchlorate with a concentration of 0.6 mol/L and N-butyl benzimidazole with a concentration of 0.4 mol/L; in the polymer P(MMA-MAh)-PEG6000, MMA is methyl methacrylate, MAh is maleic anhydride, P(MMA-MAh) is a copolymer of methyl methacrylate and maleic anhydride, and PEG6000 is polyethylene glycol with a molecular weight of 6000;

(2) adding 5 parts of dodecahydroxyl stearic acid in the primarily-mixed solution, and heating to 35° C. and reacting for 6 min under the protection of nitrogen;

(3) rinsing with deionized water and drying to obtain the polyacrylate-2-cross-linked polymer.

One or a pigment-filler mixture of titanium dioxide, kaolin and color paste may be added in the nail-care coat as needed, and then nail-care transparent coat with different colors and enough brightness is prepared.

Embodiment IV

The embodiment IV is the same as the embodiment I, but except for that the nail-care coat contains 6 parts of first composite regulator and 11 parts of second composite regulator, wherein the first composite regulator is prepared according to the formula 1 of the first composite regulator, and the second composite regulator is prepared according to the formula 1 of the second composite regulator.

The nail-care coat is prepared as follows: sequentially adding ethyl methacrylate, polydimethylsiloxane, a compound of formula I, trimethylolpropane triacrylate, polyacrylate-2-cross-linked polymer, and benzophenone; and then adding a second composite regulator and stirring for 10 min, and then adding a first composite regulator and continuously stirring for 6 min.

Embodiment V

The embodiment V is the same as the embodiment I, but except for that the nail-care coat contains 9 parts of first composite regulator and 7 parts of second composite regulator, wherein the first composite regulator is prepared according to the formula 2 of the t composite regulator, and the second composite regulator is prepared according to the formula 2 of the second composite regulator.

The nail-care coat is prepared as follows: sequentially adding ethyl methacrylate, polydimethylsiloxane, a compound of formula I, trimethylolpropane triacrylate, polyacrylate-2-cross-linked polymer, and benzophenone; and then adding a second composite regulator and stirring for 15 min, and then adding a first composite regulator and continuously stirring for 3 min.

Embodiment VI

The embodiment VI is the same as the embodiment I, but except for that the nail-care coat contains 7 parts of first composite regulator and 10 parts of second composite regulator, wherein the first composite regulator is prepared according to the formula 3 of the first composite regulator, and the second composite regulator is prepared according to the formula 3 of the second composite regulator.

The nail-care coat is prepared as follows: sequentially adding ethyl methacrylate, polydimethylsiloxane, a compound of formula I, trimethylolpropane triacrylate, polyacrylate-2-cross-linked polymer, and benzophenone; and then adding a second composite regulator and stirring for 12 min, and then adding a first composite regulator and continuously stirring for 4 min.

Embodiment VII

The embodiment VII is the same as the embodiment IV, but except for that the nail-care coat contains 3 parts of third composite regulator, wherein a preparation method for the chitosan with the deacetylation degree is as follows: carrying out heating treatment on chitin in alkaline liquor with a mass concentration of 40% for 1 h at 130° C., so as to prepare the chitosan with a deacetylation degree of 70%, and a molecular weight of 20000 Daltons. Wherein, the third composite regulator is prepared according to the formula 1 of the third composite regulator.

Embodiment VIII

The embodiment VIII is the same as the embodiment V, but except for that the nail-care coat contains 7 parts of third composite regulator, wherein a preparation method for the chitosan with the deacetylation degree is as follows: carrying out heating treatment on chitin in alkaline liquor with a mass concentration of 50% for 2 h at 150° C., so as to prepare the chitosan with a deacetylation degree of 80%, and a molecular weight of 35000 Daltons. Wherein, the third composite regulator is prepared according to the formula 2 of the third composite regulator.

Embodiment IX

The embodiment IX is the same as the embodiment VI, but except for that the nail-care coat contains 5 parts of third composite regulator, wherein a preparation method for the chitosan with the deacetylation degree is as follows: carrying out heating treatment on chitin in alkaline liquor with a mass concentration of 45% for 1.2 h at 140° C., so as to prepare the chitosan with a deacetylation degree of 78%, and a molecular weight of 25000 Daltons. Wherein, the third composite regulator is prepared according to the formula 3 of the third composite regulator.

Embodiment X

The embodiment X is the same as the embodiment VII, but except for that the nail-care coat contains 1 part of fourth composite regulator, wherein, the fourth composite regulator is prepared according to the formula 1 of the fourth composite regulator.

A preparation method for the second elastic gum is as follows: heating 1 part of polyvinyl alcohol aqueous solution with a mass concentration of 20% and 20 parts of 15 wt % waterborne polyurethane aqueous solution to 60° C., cooling to 30° C. and adding 10 parts of acrylate, then adding 0.1 part of lithium hydroxide and heating to 100° C., then adding 5 parts of sclerotin protein, 6 parts of abietin and 2 parts of eugenol; and reacting for 3 hours and cooling to 45° C., then adding 6 parts of bamboo charcoal micro-powder, 2 parts of anion powder and 13 parts of octylphenol polyoxyethylene ether, stirring for 1 hour, and cooling to prepare the second elastic gum.

The nail-care coat is prepared as follows: sequentially adding ethyl methacrylate, polydimethylsiloxane, 0.05 part of compound of formula I, trimethylolpropane triacrylate, polyacrylate-2-cross-linked polymer, and benzophenone; and then adding a second composite regulator and stirring for 10 min, and then adding a first composite regulator and continuously stirring for 3 min; then adding a fourth composite regulator and continuously stirring for 2 min; and finally adding a third composite regulator and continuously stirring for 1 min, and filtering and packaging to obtain the finished product.

Embodiment XI

The embodiment XI is the same as the embodiment VIII, but except for that the nail-care coat contains 1-4 parts of fourth composite regulator, wherein, the fourth composite regulator is prepared according to the formula 2 of the fourth composite regulator.

A preparation method for the second elastic gum is as follows: heating 5 parts of polyvinyl alcohol aqueous solution with a mass concentration of 25% and 30 parts of 20 wt % waterborne polyurethane aqueous solution to 80° C., cooling to 50° C. and adding 15 parts of acrylate, then adding 0.2 part of lithium hydroxide and heating to 110° C., then adding 8 parts of sclerotin protein, 9 parts of abietin and 4 parts of eugenol; and reacting for 5 hours and cooling to 55° C., then adding 8 parts of bamboo charcoal micro-powder, 7 parts of anion powder and 10 parts of octylphenol polyoxyethylene ether, stirring for 1.5 hours, and cooling to prepare the second elastic gum.

The nail-care coat is prepared as follows: sequentially adding ethyl methacrylate, polydimethylsiloxane, 0.04 part of compound of formula I, trimethylolpropane triacrylate, polyacrylate-2-cross-linked polymer, and benzophenone; and then adding a second composite regulator and stirring for 15 min, and then adding a first composite regulator and continuously stirring for 6 min; then adding a fourth composite regulator and continuously stirring for 5 min; and finally adding a third composite regulator and continuously stirring for 4 min, and filtering and packaging to obtain the finished product.

Embodiment XII

The embodiment XII is the same as the embodiment IX, but except for that the nail-care coat contains 3 parts of fourth composite regulator, wherein, the fourth composite regulator is prepared according to the formula 3 of the fourth composite regulator.

A preparation method for the second elastic gum is as follows: heating 2 parts of polyvinyl alcohol aqueous solution with a mass concentration of 22% and 25 parts of 18 wt % waterborne polyurethane aqueous solution to 66° C., cooling to 33° C. and adding 12 parts of acrylate, then adding 0.12 part of lithium hydroxide and heating to 105° C., then adding 6 parts of sclerotin protein, 7 parts of abietin and 3 parts of eugenol; and reacting for 4 hours and cooling to 49° C., then adding 7 parts of bamboo charcoal micro-powder, 5 parts of anion powder and 12 parts of octylphenol polyoxyethylene ether, stirring for 1.2 hours, and cooling to prepare the second elastic gum.

The nail-care coat is prepared as follows: sequentially adding ethyl methacrylate, polydimethylsiloxane, 0.03 part of compound of formula I, trimethylolpropane triacrylate, polyacrylate-2-cross-linked polymer, and benzophenone; and then adding a second composite regulator and stirring for 12 min, and then adding a first composite regulator and continuously stirring for 4 min. Then adding a fourth composite regulator and continuously stirring for 3 min; and finally adding a third composite regulator and continuously stirring for 2 min, and filtering and packaging to obtain the finished product.

Embodiment XIII

The embodiment XIII is the same as the embodiment X, but except for that the first composite regulator is prepared according to the formula 1 of the first composite regulator; the second composite regulator is prepared according to the formula 2 of the second composite regulator; the third composite regulator is prepared according to the formula 3 of the third composite regulator; and the fourth composite regulator is prepared according to the formula 1 of the fourth composite regulator.

Embodiment XIV

The embodiment XIV is the same as the embodiment XI, but except for that the first composite regulator is prepared according to the formula 1 of the first composite regulator the second composite regulator is prepared according to the formula 3 of the second composite regulator; the third composite regulator is prepared according to the formula 2 of the third composite regulator; and the fourth composite regulator is prepared according to the formula 2 of the fourth composite regulator.

Embodiment XV

The embodiment XV is the same as the embodiment XI, but except for that the first composite regulator is prepared according to the formula 2 of the first composite regulator; the second composite regulator is prepared according to the formula 1 of the second composite regulator; the third composite regulator is prepared according to the formula 3 of the third composite regulator; and the fourth composite regulator is prepared according to the formula 3 of the fourth composite regulator.

Activity Experiments:

1. Activity Experiment on the Compound of Formula I

Bacteria (*trichophylon rubrum*, *trichophyton mentagrophytes* and *epidermophyton fioccosum*) are suspended in an MH culture medium with a dispersion concentration of about $10^5$ cfu·$ML^{-1}$, and bacterium solution is added onto a 96-well plate (100 μL of the bacterium solution is added in each well); and the culture medium is taken as blank control, DMSO is taken as negative control for replacing a test substance, and itraconazole (Xian-Janssen Pharmaceutical Co., Ltd.) is taken as positive control. The compound of formula I is dissolved in the DMSO and prepared into solution with concentrations of 800 μg·$ML^{-1}$, 400 μg·$ML^{-1}$, 200 μg·$ML^{-1}$, 100 μg·$ML^{-1}$, 50 μg·$ML^{-1}$ and 25 μg·$ML^{-1}$ respectively (for the solution with $MIC_{50}$ of less than 5 μg·$ML^{-1}$, during a one-step experiment, the concentration gradients of the prepared solution are 50 μg·$ML^{-1}$, 25 μg·$ML^{-1}$, 12.5 μg·$ML^{-1}$, 6.25 μg·$ML^{-1}$, 3.1 μg·$ML^{-1}$ and 1.5 μg·$ML^{-1}$); the solution is added onto the 96-well plate according to an amount of 11 μL in each well [the final concentrations of the chemical solution are 80 μg·$ML^{-1}$, 40 μg·$ML^{-1}$, 20 μg·$ML^{-1}$, 10 μg·$ML^{-1}$, 5 μg·$ML^{-1}$ and 2.5 μg·$ML^{-1}$ respectively (for the latter, the final concentrations are 5 μg·$ML^{-1}$, 2.5 μg·$ML^{-1}$, 1.25 μg·$ML^{-1}$, 0.63 μg·$ML^{-1}$, 0.31 μg·$ML^{-1}$ and 0.15 μg·$ML^{-1}$)]; and four parallel experiments are carried out with regard to each concentration gradient. The 96-well plate is placed in an incubator at 37° C. and cultured for 24 h, then 25 μL of PBS containing 4 mg of MTT per mL is added in each well and cultured for 4 h under the same condition, and 100 μL of SDS lysate (95 mL of tri-distilled water+10 g of SDS+5 mL of isopropanol+0.1 mL of concentrated hydrochloric acid) is added in each well and then cultured for 12 h. An OD value is measured by a microplate reader at 570 nm, and an inhibition percent is calculated as follows:

$$I\% = 100 - \frac{OD_{Test}}{OD_{Control}} \times 100.$$

The level of activity is represented by a 50% minimum inhibitory concentration ($MIC_{50}$), the lower the $MIC_{50}$ is, the higher the activity of the compound is, and the result is: the 50% minimum inhibitory concentrations ($MIC_{50}$) of the compound of formula I for *trichophyton rubrum*, *trichophyton mentagrophytes* and *epidennophyton floccosum* are 0.63, 0.60 and 0.82 respectively; and the 50% minimum inhibitory concentrations ($MIC_{50}$) of the itraconazole for *trichophyton rubrum*, *trichophyton mentagrophytes* and *epidermophyton floccosum* mare 0.63, 0.70 and 0.65 respectively.

2. Activity Experiment on Preparations:

The preparations in the embodiments 1-5 are used for carrying out the following activity experiment:

a small piece with a thickness of about 0.5 mm and a size of 1.5 cm×3 cm is cut from the corner of an ox horn, half of a side surface is treated with the preparations in the embodiments 1-5 once every day, and the treatment is carried out for five consecutive days. Then the piece is fixed on a metal column which is about 0.5 cm above the surface of water-containing agar in a moist chamber, and the half of the treated side surface is downward. A microconidium suspension of *trichophyton mentagrophytes* is inoculated on the whole upward side surface of the ox horn in the form of points. Then the microconidium suspension is stored for 10 days at 28° C. in the form of colonies.

Sprouting of fungal spores on the whole top surface is completely prevented by using the preparations in the embodiments 1-5 of the present invention for pre-treating half of the back surface of the ox horn for 5 times. The inoculated points cannot be observed on the whole top surface under a microscope even after 90 days. Therefore, fungal growth can be effectively prevented by the preparations in the embodiments 1-5, which contain the compound of formula I.

A control experiment is carried out according to the above-mentioned method, and the difference lies in that the compound of formula is not contained in all the preparations in the embodiments 1-5, there are a few of growth points of fungi on the treated side surface of the ox horn, however, good growth of fungi is observed on the other half of the piece.

After a blank piece which is not treated by the preparations in the present invention is inoculated, fungi grow sufficiently on the surface of the ox horn.

In case of being applied onto nails, the nail-care coat disclosed by the present invention is healthy and environment-friendly, and without a pungent smell, can be cured to form a film only by being subjected to normal-temperature drying for 1 to 3 minutes or subjected to LED light curing for 1 to 2 minutes, and has a transparent diamond-like gloss: in case of color change, the nail-care coat only needs to be peeled away from nail tips and then torn; and the nail-care coat disclosed by the present invention is a two-in-one product composed of a prime coat and a top coat, and is capable of being peeled or torn as a whole, without the need of washing and without residue. Moreover, the compound of formula I is used in the nail-care coat disclosed by the present invention, and is capable of effectively preventing and controlling invasion of fungi.

I claim:

1. A peelable transparent nail-care composition, characterized by containing the following components in parts by weight:

40-50 parts of polyacrylate-2 crosspolymer, 5-12 parts of benzophenone, 20-30 parts of ethyl methacrylate, 8-16 parts of polydimethylsiloxane, 0.01-0.05 part of a compound of formula I, and 10-15 parts of trimethylolpropane triacrylate, wherein the compound of formula I is shown as the following formula:

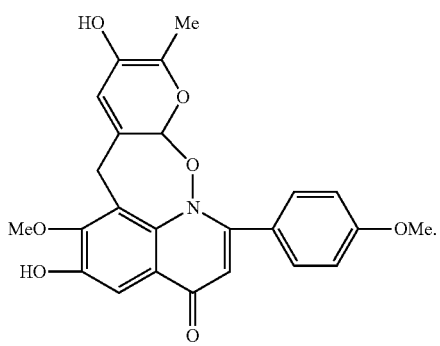

2. The nail-care composition according to claim 1, characterized in that the nail-care composition contains titanium dioxide, kaolin, color paste or combinations thereof.

3. The nail-care composition according to claim 1, characterized in that: the nail-care composition contains 6-9 parts of a first composite regulator and 7-11 parts of a second composite regulator;
the first composite regulator comprises a mixture composed of polyglycerol-2-triisostearate, glycerol and ammonium acryloyldimethyltaurate according to a mass ratio of 1:(3 to 4):(1 to 2); and
the second composite regulator comprises a mixture composed of diisostearyl malate, silica silylate and butyl methoxydibenzoylmethane according to a mass ratio of 1:(2 to 4):(1 to 3).

4. The nail-care composition according to claim 3, characterized in that: the nail-care composition contains 3-7 parts of third composite regulator; and the third composite regulator comprises a mixture composed of chitosan with a deacetylation degree of 70%-80%, an oligosaccharide with a molecular weight of 1800 Daltons-2000 Daltons, and dipropylene glycol monobutylether according to a mass ratio of 1:(0.5 to 0.8):(1.3 to 1.7).

5. The nail-care composition according to claim 4, wherein the chitosan is prepared by carrying out a heating treatment in an alkaline liquor with a mass concentration of 40%-50% for 1 h-2 h at 130° C.-150° C., so as to prepare the chitosan with a deacetylation degree of 70%-80%, and a molecular weight of 20000 Daltons-35000 Daltons.

6. The nail-care composition according to claim 1, wherein the polyacrylate-2-crosspolymer is prepared by:
(1) preparing, in parts by weight, 30-40 parts of polymer P(MMA-MAh)-PEG 6000 and 40-60 parts of regulating solution to form a primarily-mixed solution: the regulating solution is propylene carbonate solution comprising sodium perchlorate with a concentration of 0.4 mol/L-0.7 mol/L and N-butyl benzimidazole with a concentration of 0.3 mol/L-0.8 mol/L; in the polymer P(MMA-MAh)-PEG 6000, MMA is methyl methacrylate, MAh is maleic anhydride, P(MMA-MAh) is a copolymer of methyl methacrylate and maleic anhydride, and PEG 6000 is polyethylene glycol with a molecular weight of 6000;
(2) adding 2-7 parts of dodecahydroxyl stearic acid in the primarily-mixed solution, and heating to 30° C.-45° C. and reacting for 5 min-9 min under the protection of nitrogen;
(3) rinsing with deionized water and drying to obtain the polyacrylate-2-crosspolymer.

7. The nail-care composition according to claim 6, characterized in that: the nail-care composition contains 1-4 parts of a fourth composite regulator: and the fourth composite regulator is composed of the following materials in parts by weight: 25-35 parts of cetyl octanoate, 15-18 parts of glutaric acid, 8-10 parts of butantriol, 5-7 parts of zinc oxide, 3-5 parts of magnesium oxide, 15-25 parts of chloroprene rubber, 70-95 parts of elastic gum, 15-20 parts of dimethyl carbonate and 20-30 parts of ethylbenzene; the elastic gum comprises a first elastic gum and a second elastic gum which are mixed according to a weight ratio of 1:(2 to 5); the first elastic gum comprises 10-35 parts by weight of acrylic resin emulsion with a solid content of 60%-75%, 10-15 parts of waterborne polyurethane, 5-8 parts by weight of acrylic resin powder, 2-6 parts by weight of ethylene vinyl acetate emulsion with a solid content of 20%-35% and 1-4 parts by weight of chlorinated polypropylene;
a preparation method for the second elastic gum is as follows: heating 1-5 parts of polyvinyl alcohol aqueous solution with a mass concentration of 20%-25% and 20-30 parts of 15 wt %-20 wt % waterborne polyurethane aqueous solution to 60° C.-80° C., cooling to 30° C.-50° C. and adding 10-15 parts of acrylate, then adding 0.1-0.2 part of lithium hydroxide and heating to 100° C.-110° C., then adding 5-8 parts of sclerotin protein, 6-9 parts of abietin and 2-4 parts of eugenol; and reacting for 3 to 5 hours and cooling to 45° C.-55° C., then adding 6-8 parts of bamboo charcoal micropowder, 2-7 parts of anion powder and 10-13 parts of octylphenol polyoxyethylene ether, stirring for 1 to 1.5 hours, and cooling to prepare the second elastic gum.

8. A preparation method for the peelable transparent diamond nail-care composition according to claim 1, characterized by comprising the steps of sequentially adding
20-30 parts of ethyl methacrylate
8-16 parts of polydimethylsiloxane,
0.01-0.05 part of compound of formula I,
10-15 parts of trimethylolpropane triacrylate,
40-50 parts of polyacrylate-2-crosspolymer, and
5-12 parts of benzophenone, and
mixing the above-mentioned ingredients, and then uniformly stirring and mixing at a high speed to prepare the nail-care composition.

9. The preparation method according to claim 8, characterized in that: after the above-mentioned substances are added in sequence, a second composite regulator is added and stirred for 10 min-15 min, and then a first composite regulator is added and stirred continuously for 3 min-6 min; then a fourth composite regulator is added and stirred continuously for 2 min-5 min; and finally a third composite regulator is added and stirred continuously for 1 min-4 min, and filtering and packaging are carried out to obtain the finished product.

* * * * *